US009838807B2

(12) United States Patent
Jinton et al.

(10) Patent No.: US 9,838,807 B2
(45) Date of Patent: *Dec. 5, 2017

(54) BONE ANCHOR FIXTURE FOR A MEDICAL PROSTHESIS

(71) Applicant: Cochlear Limited, Macquarie University, NSW (AU)

(72) Inventors: Lars Jinton, Mölndal (SE); Erik Holgersson, Gothenburg (SE); Peter Elmberg, Kållered (SE)

(73) Assignee: Cochlear Limited, Macquarie University, NSW (AU)

( * ) Notice: Subject to any disclaimer, the term of this patent is extended or adjusted under 35 U.S.C. 154(b) by 69 days.

This patent is subject to a terminal disclaimer.

(21) Appl. No.: 14/922,604

(22) Filed: Oct. 26, 2015

(65) Prior Publication Data

US 2016/0038202 A1 Feb. 11, 2016

Related U.S. Application Data

(63) Continuation of application No. 12/177,083, filed on Jul. 21, 2008, now Pat. No. 9,173,042.

(Continued)

(51) Int. Cl.
*A61B 17/00* (2006.01)
*H04R 25/00* (2006.01)
(Continued)

(52) U.S. Cl.
CPC ......... *H04R 25/606* (2013.01); *A61B 17/863* (2013.01); *A61B 17/8615* (2013.01);
(Continued)

(58) Field of Classification Search
CPC ............................ A61B 17/863; H04R 25/606
See application file for complete search history.

(56) References Cited

U.S. PATENT DOCUMENTS 2,016,610 A 10/1935 Moeller
2,347,567 A * 4/1944 Kresse ................ A61C 8/0022
424/487

(Continued)

FOREIGN PATENT DOCUMENTS

EP 0996391 B1 2/2004
KR 20120000235 A 1/2012
(Continued)

OTHER PUBLICATIONS

Extended European Search Report for European Application No. 08782157.5 dated Jan. 2, 2013.
(Continued)

*Primary Examiner* — Christian Sevilla
(74) *Attorney, Agent, or Firm* — Hauptman Ham, LLP; Martin J. Cosenza

(57) ABSTRACT

A screw-shaped anchoring fixture for anchoring a prosthesis in the skull bone. The anchoring fixture comprises a main body configured to be implanted into the bone and a flange configured to function as a stop to prevent the main body from completely penetrating through the bone. The main body comprises a distal tapered apical portion, a first portion, and a second portion. The inner diameter of the second portion is greater than the inner diameter of the first portion. The method for inserting the anchoring fixture includes providing the anchoring fixture, drilling a hole, and inserting the anchoring fixture into the hole until the flange contacts the skull bone, wherein the hole has a diameter that is greater than the inner diameter of the first portion and less than the outer diameter of the second portion.

48 Claims, 2 Drawing Sheets

Related U.S. Application Data

(60) Provisional application No. 60/951,169, filed on Jul. 20, 2007, provisional application No. 60/951,163, filed on Jul. 20, 2007.

(51) Int. Cl.
*A61C 8/00* (2006.01)
*A61B 17/86* (2006.01)

(52) U.S. Cl.
CPC .......... *A61C 8/0025* (2013.01); *A61C 8/0066* (2013.01); *A61C 8/0069* (2013.01); *H04R 2460/13* (2013.01)

(56) References Cited

U.S. PATENT DOCUMENTS

| | | | |
|---|---|---|---|
| 4,025,964 A | 5/1977 | Owens | |
| 4,498,461 A * | 2/1985 | Hakansson | H04R 25/606 |
| | | | 181/126 |
| D294,295 S | 2/1988 | Branemark | |
| 4,738,623 A | 4/1988 | Driskell | |
| 4,904,233 A | 2/1990 | Hakansson et al. | |
| 4,917,555 A | 4/1990 | Taubert | |
| 4,936,317 A | 6/1990 | MacGregor | |
| 4,998,461 A | 3/1991 | Ishiwata et al. | |
| 5,135,395 A | 8/1992 | Marlin | |
| 5,269,685 A * | 12/1993 | Jorneus | A61C 8/0022 |
| | | | 433/173 |
| 5,588,883 A | 12/1996 | Hattori | |
| 5,653,710 A | 8/1997 | Harle | |
| 5,735,790 A * | 4/1998 | Håkansson | H04R 25/606 |
| | | | 600/25 |
| 5,769,630 A | 6/1998 | Hoffman | |
| 5,833,463 A | 11/1998 | Hurson | |
| 5,885,079 A * | 3/1999 | Niznick | A61C 8/0022 |
| | | | 433/174 |
| 5,961,329 A | 10/1999 | Stucki-McCormick | |
| 6,030,162 A | 2/2000 | Huebner | |
| 6,086,303 A | 7/2000 | Fluckiger | |
| 6,468,277 B1 * | 10/2002 | Justin | A61B 17/863 |
| | | | 606/304 |
| 6,474,991 B1 | 11/2002 | Hansson | |
| 6,604,945 B1 | 8/2003 | Jones | |
| 6,643,378 B2 | 11/2003 | Schumaier | |
| 6,669,701 B2 | 12/2003 | Stiener et al. | |
| 6,840,919 B1 | 1/2005 | Hakansson | |
| 6,896,517 B1 | 5/2005 | Bjorn et al. | |
| 6,953,463 B2 | 10/2005 | West, Jr. | |
| 7,065,223 B2 | 6/2006 | Westerkull | |
| 7,074,222 B2 | 7/2006 | Westerkull | |
| 7,806,693 B2 | 10/2010 | Hurson | |
| D634,186 S | 3/2011 | Kemper | |
| 8,016,593 B2 | 9/2011 | Hall | |
| 8,170,252 B2 | 5/2012 | Parker et al. | |
| 2003/0176866 A1 * | 9/2003 | Westerkull | A61F 2/141 |
| | | | 606/312 |
| 2004/0032962 A1 | 2/2004 | Westerkull | |
| 2004/0152047 A1 | 8/2004 | Odrich et al. | |
| 2004/0210103 A1 | 10/2004 | Westerkull | |
| 2004/0228705 A1 | 11/2004 | Baer et al. | |
| 2005/0106534 A1 | 5/2005 | Gahlert | |
| 2005/0153261 A1 | 7/2005 | Chang | |
| 2005/0248158 A1 | 11/2005 | Westerkull | |
| 2005/0249366 A1 | 11/2005 | Westerkull | |
| 2005/0250074 A1 | 11/2005 | Lang et al. | |
| 2005/0287497 A1 | 12/2005 | Carter | |
| 2006/0050913 A1 * | 3/2006 | Westerkull | H04R 25/606 |
| | | | 381/326 |
| 2006/0056649 A1 | 3/2006 | Schumaier | |
| 2006/0093175 A1 * | 5/2006 | Westerkull | H04R 25/606 |
| | | | 381/326 |
| 2006/0126874 A1 | 6/2006 | Westerkull | |
| 2006/0172257 A1 | 8/2006 | Niznick | |
| 2006/0195099 A1 | 8/2006 | Bottlang | |
| 2006/0211910 A1 | 9/2006 | Westerkull | |
| 2007/0009853 A1 | 1/2007 | Pitulia | |
| 2007/0053536 A1 | 3/2007 | Westerkull | |
| 2007/0059666 A1 | 3/2007 | Zickman et al. | |
| 2007/0147973 A1 | 6/2007 | Laan | |
| 2008/0032264 A1 | 2/2008 | Hall | |
| 2009/0023109 A1 | 1/2009 | Jinton et al. | |
| 2009/0082817 A1 | 3/2009 | Jinton et al. | |
| 2010/0240010 A1 | 9/2010 | Holmstrom | |
| 2010/0249784 A1 | 9/2010 | Andersson | |
| 2010/0286776 A1 | 11/2010 | Andersson | |
| 2011/0195380 A1 | 8/2011 | Giomo | |
| 2012/0143251 A1 | 6/2012 | Green et al. | |
| 2015/0215696 A1 | 7/2015 | Bjorn et al. | |

FOREIGN PATENT DOCUMENTS

| | | |
|---|---|---|
| SE | 531177 C2 | 1/2009 |
| WO | 9205745 A1 | 4/1992 |
| WO | 9619950 A1 | 7/1996 |
| WO | 9855049 A1 | 12/1998 |
| WO | 9923971 A1 | 5/1999 |
| WO | 0193634 A1 | 12/2001 |
| WO | 0193645 A1 | 12/2001 |
| WO | 0209622 A1 | 2/2002 |
| WO | 2004012622 A1 | 2/2004 |
| WO | 2004045432 A1 | 6/2004 |
| WO | 2004058091 A1 | 7/2004 |
| WO | 2004093401 A1 | 10/2004 |
| WO | 2004098442 A1 | 11/2004 |
| WO | 2004105650 A1 | 12/2004 |
| WO | 2005000391 A1 | 1/2005 |
| WO | 2006052527 A2 | 5/2006 |
| WO | 2009015102 A1 | 1/2009 |
| WO | 2009015103 A1 | 1/2009 |

OTHER PUBLICATIONS

Extended European Search Report for European Application No. 08782159.1 dated Jan. 3, 2013.
Sjostrom et al., "Monitoring of implant stability in grafted bone using resonance frequency analysis—A clinical study from implant placement to 6 months of loading", Jan. 2005, pp. 45-51, vol. 34, issue 1.
http://www.merriam-webster.com/dictionary/tapered, Retrieved Apr. 10, 2012.
http://www.merriam-webster.com/dictionary/apical, Retrieved Apr. 10, 2012.
http://www.merriam-webster.com/dictionary/portion, Retrieved Apr. 10, 2012.
Written Opinion for PCT/US2008/070679, dated Oct. 15, 2008.
International Preliminary Report on Patentability for PCT/US2008/070681, dated Aug. 21, 2009.
Written Opinion for PCT/US2008/070681, dated Dec. 15, 2008.
Mats Thomsson et al., "A retrospective case series evaluating Branemark BioHelix implants placed in a specialist private practice following 'conventional' procedures. One-year results after placement," Eur J Oral Implantol., Oct. 2008, pp. 229-234, vol. 1, No. 3.

* cited by examiner

BONE ANCHOR FIXTURE FOR A MEDICAL PROSTHESIS

CROSS-REFERENCE TO RELATED APPLICATIONS

The present application is a Continuation application of U.S. patent application Ser. No. 12/177,083, filed Jul. 21, 2008, naming Lars Jinton as an inventor, which claims the benefit of U.S. Provisional Application No. 60/951,163, filed Jul. 20, 2007, and U.S. Provisional Application No. 60/951,169, filed Jul. 20, 2007. The entire contents of these applications are incorporated herein by reference in their entirety.

BACKGROUND

Filed of the Invention

The present invention relates generally to hearing devices and, more particularly, to anchoring elements for bone anchored hearing devices.

Related Art

For persons who cannot benefit from traditional, air conduction hearing aids there are other types of hearing aids on the market commonly referred to as bone anchored hearing aids. Bone anchored hearing aids mechanically transmit sound information to a person's inner ear via the skull bone by means of a vibrator. Such hearing aid devices are typically connected to a percutaneous implant in the form of a titanium screw implanted in the skull bone behind the external ear so that sound is transmitted via the skull bone to the cochlea (inner ear). This enables the hearing aid to be effective regardless of whether there is disease or damage in the middle ear. Moreover, penetration of the skin makes the vibratory transmission very efficient.

Bone anchored hearing aids were initially developed to rehabilitate certain types of hearing-impaired patients. They may also be utilized for other indications such as stuttering and for certain non-medical applications. A bone anchored hearing aid may be connected to an implant by means of a bayonet coupling, a snap-in coupling, a magnetic coupling or the like. One example of this type of hearing aid device is the BAHA® bone anchored hearing aid, described in U.S. Pat. No. 4,498,461 and commercially available from Cochlear Bone Anchored Solutions AB (previously Entific Medical Systems AB) in Göteborg, Sweden.

The implant connecting the hearing aid to the skull generally comprises two components: a bone attachment piece that is attached or implanted directly into the skull bone and a skin penetrating piece coupled to the bone attachment piece. The reason for this two-piece design is that installation of the implant is occasionally performed in two steps. In the first step, the bone attachment piece is installed and the surrounding issue is allowed to heal for a period of time that may last up to a few months. In the second step, the skin penetrating piece is coupled to the bone attachment piece. In the event that the skin penetrating piece becomes damaged, it may be replaced without removing the anchoring fixture from the skull. Moreover, the hearing aid may be changed or upgraded if necessary, without removing the bone attachment piece from the skull.

Although conventional fixtures normally provide a certain degree of osseo-integration, a more effective integration between the implant screw and the skull bone is desired, for example, for patients having impaired bone quality. Moreover, loading of the implant at an earlier stage would also be desired.

SUMMARY

In one embodiment, an anchoring fixture for anchoring a prosthesis to a skull bone is disclosed. The anchoring fixture comprises a main body configured to be implanted into the skull bone. The main body further comprises a distal tapered apical portion and a first portion adjacent to the distal tapered apical portion. The main body also comprises a second portion adjacent to the first portion. The first portion has a first inner diameter and the second portion has a second inner diameter that is greater than the first inner diameter. This configuration provides compression in the radial direction on the skull bone to improve the initial stability of the anchoring fixture.

In another embodiment, an anchoring fixture for anchoring a prosthesis to a skull bone is disclosed. The anchoring fixture comprises a main body configured to be implanted into the skull bone and a flange. The main body further comprises a distal tapered apical portion and a first threaded portion having a first diameter adjacent to the distal apical portion and an adjacent second threaded portion having a second diameter. The second diameter is greater than the first diameter. The flange is adjacent to the second threaded portion, the flange comprising a planar bottom surface adapted to rest on top of the skull bone when the main body is implanted into the skull bone.

In yet another embodiment, an anchoring fixture for anchoring a prosthesis to a skull bone is disclosed. The anchoring fixture comprises an implantation means for securing the anchoring fixture onto the skull bone without completely penetrating through the skull bone. The implantation means comprises a compression means for exerting a compression onto the skull bone in a radial direction to stabilize the fixture in the skull bone.

In a further embodiment, a method for installing the anchoring fixture into a skull bone is disclosed. The method comprises providing an anchoring fixture, drilling a hole into the skull bone and inserting the anchoring fixture in the hole until the flange contacts the skull bone, wherein the hole has a diameter that is greater than the inner diameter of the first portion and less than the outer diameter of the second portion. In one aspect of the embodiment, the inserting step comprises screwing the anchoring fixture into the skull bone.

BRIEF DESCRIPTION OF THE DRAWINGS

Embodiments of the present invention are described herein with reference to the accompanying drawings, in which.

Like numerals refer to like parts throughout the several views of the drawings.

DETAILED DESCRIPTION OF THE INVENTION

Aspects of the various embodiments disclosed herein are generally directed to providing screw-shaped anchoring fixtures configured to be anchored in the comparatively thin skull bone and having a certain compressive ability in the radial direction to improve the initial stability of the fixture.

In one embodiment, the anchoring fixture has a main body configured to be inserted in the skull bone and a flange configured to prevent the fixture from completely penetrating through the skull bone. The main body comprises a first and second substantially cylindrical portion. The first portion comprises a screw thread having a first inner diameter and the second portion is adjacent to the flange and has a second inner diameter that is greater than the first inner diameter. Preferably, the second portion has at least one groove extending around the periphery of the cylindrical portion. The groove may have a bottom diameter exceeding the first inner diameter of the screw thread. Preferably, the groove forms a second screw thread having an inner diameter exceeding the inner diameter of the first, main screw thread. The surface of at least the first portion of the main body may be modified to increase the surface roughness.

In another embodiment, a method for inserting the anchoring fixture is disclosed. In accordance with one aspect of this embodiment, a drill may be used to drill a hole in the skull bone before installing the anchoring fixture. The drill creates a hole in the skull bone having a diameter which is larger than the inner diameter of the screw thread of the first cylindrical portion, but less than the outer diameter of the second cylindrical portion. When the fixture is inserted into the drilled hole, the wider second portion of the fixture, i.e. the portion next to the flange, provides a certain compression to the bone, specifically the cortical bone, in the radial direction of the hole.

Figure 1:
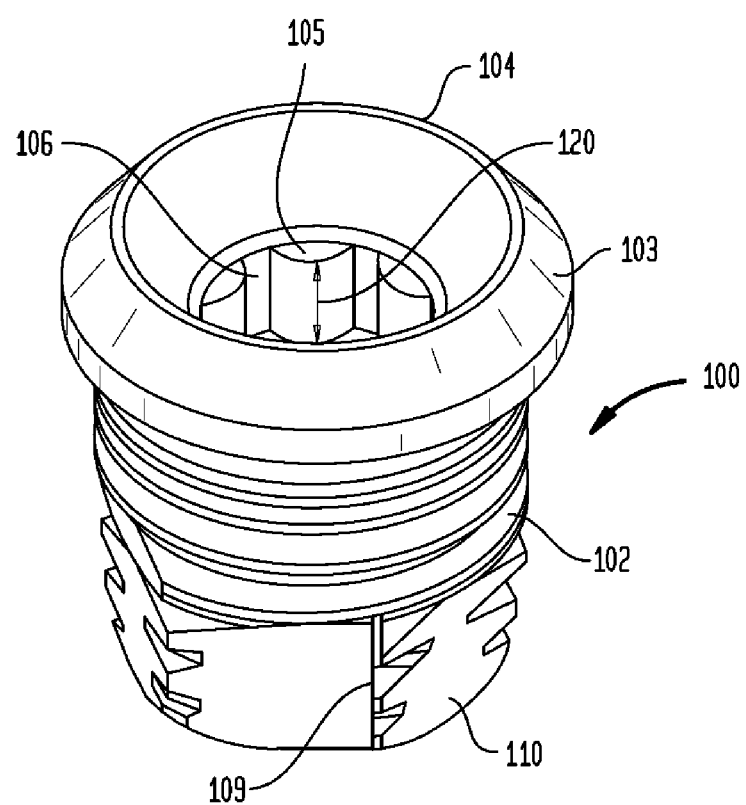
FIG. 1 is a perspective view of an anchoring element in accordance with one embodiment of the anchoring fixture.

Embodiments of the bone anchored coupling apparatus will be described below with reference to the accompanying drawings. FIG. 1 illustrates an example of a screw-shaped anchoring fixture 100 in accordance with one embodiment. Fixture 100 is preferably made of any biocompatible material that has a known ability to integrate with the surrounding bone tissue, a phenomenon commonly referred to as osseointegration. In one embodiment, fixture 100 is made of titanium. Fixture 100 has a main body 102 configured to be implanted into the skull bone, a flange 103 configured to serve as a stop to prevent fixture from penetrating through the skull bone, and a tool engaging socket 104 in the form of an internal grip section 105 for easy lifting and handling of fixture 100. The geometrical configuration of the internal grip section may be configured in a manner that allows for engagement with an insertion tool. In accordance with one aspect, the geometric configuration may be in the form of a hex, multi-lobed surfaces, slots or grooves. As shown in FIG. 1 a number of lobe-shaped surfaces 106 is provided in the internal grip section and extends a distance or height (H) 120 in the longitudinal direction of the main body of the fixture parallel to longitudinal axis 107 of the fixture. The lobe-shaped surfaces 106 may be configured to cooperate with an insertion tool having slightly tapered engaging surfaces to engage and lift the fixture.

Figure 2:
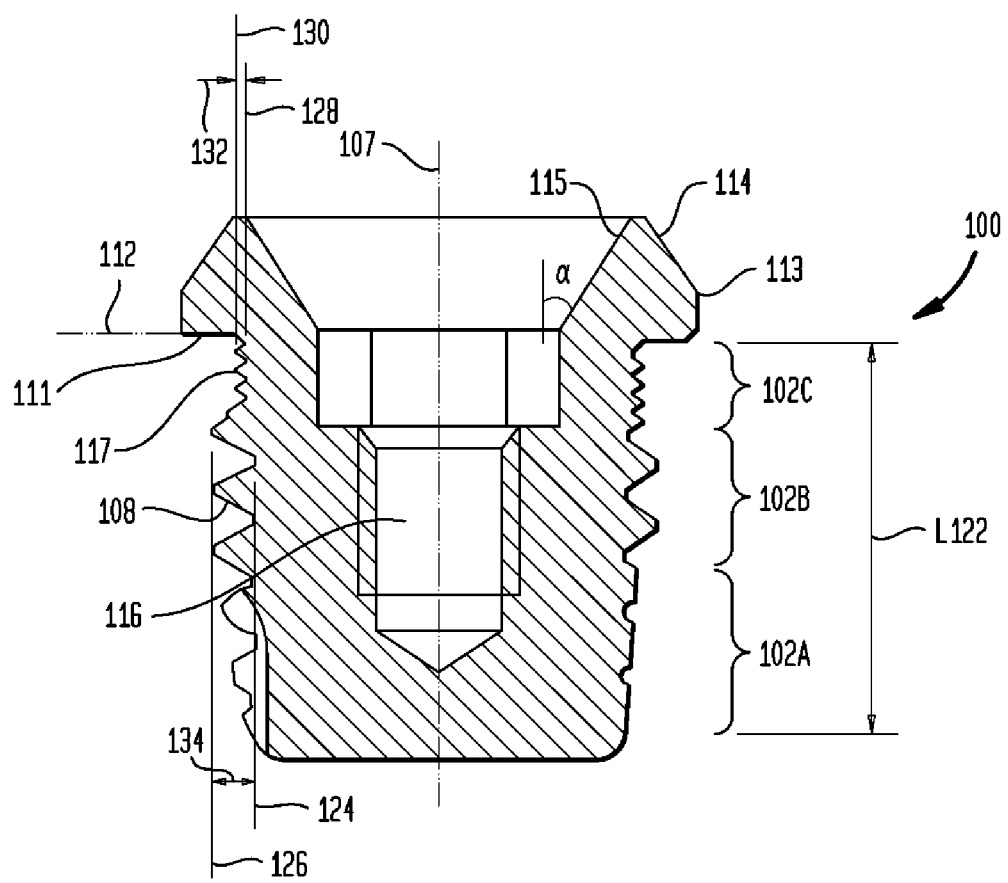
FIG. 2 is a cross-sectional side view of the anchoring element illustrated in FIG. 1.

The main body 102 has a length sufficient to securely anchor fixture 100 into, without penetrating entirely through, the skull bone. The length of main body 102 may therefore depend on the thickness of the skull bone at the implantation site. In one embodiment, main body 102 has a length (L) 122 no greater than approximately 5 mm. Main body 102 further comprises a distal tapered apical portion 102A and a straight, generally cylindrical body comprising two portions, a first portion 102B and a second portion 102C. First portion 102B comprises external threads that form the main screw thread 108 adjacent to the distal tapered apical portion. The second portion 102C is adjacent to the flange. As illustrated in FIG. 2, main screw thread 108 has an inner diameter 124 and an outer diameter 126. In one embodiment, the outer diameter 126 is approximately 3.5-5.0 mm.

As further shown in FIGS. 1 and 2, the distal tapered apical part 102A of main body 102 is configured with self-tapping cutting edges 109. Additional information regarding the self-tapping action is described in greater detail in WO 02/09622, which is hereby incorporated by reference herein. Clearance or relief surfaces 110 may also be provided, wherein the self-tapping cutting edges 109 and the clearance or relief surfaces 110 are provided in an alternating configuration around the main body periphery. This alternating configuration is advantageous because it creates more volume for the cut-off bone chips and therefore reduces the squeezing effect between the fixture 100 and the bone during installation.

As more clearly illustrated in FIG. 2, flange 103 has a planar bottom surface 111 for resting against the outer bone surface, indicated by 112, when the fixture 100 has been screwed into the skull bone. Again, flange 103 prevents the fixture 100 from completely penetrating through the skull bone. Preferably, flange 103 has a diameter which exceeds the peak diameter of the threads by approximately 10-20%. The outer peripheral surface of the flange has a cylindrical part 113 and a tapered top portion 114. The upper end of the flange is designed with an open cavity with a tapered inner side wall 115, a grip section 105, and an inner bottom bore 116 with an internal screw thread for directly or indirectly connecting a hearing aid device or any orbital or ear prosthesis. In order to achieve a stable connection, the inner opening and bore extends to the bottom half of the main body of the fixture 100. The tapered inner side wall 115 forms a seat for a skin-penetrating abutment or the like to create a good connecting fit between the two parts fixture and abutment. The cone angle α may be in the range of about 30-40 degrees. However, the connection with abutment and other parts in the system are not part of this invention and will not be described in any detail here.

In one embodiment, no protruding hex is provided in the embodiment depicted in FIGS. 1 and 2. Rather, the flange forms a smooth, open upper end. The smooth upper end of flange 103 and the absence of any sharp corners provides for improved soft tissue adaptation. Flange 103 also comprises a cylindrical part 113 and a flared top portion 114 which provide sufficient height in the longitudinal direction for internal connection with an abutment sleeve (not shown).

FIG. 2 shows the second portion 102C adjacent to flange 103 having an inner diameter 128 which exceeds the inner diameter 124 of the main threads 108 of the first portion 102B. As noted, this configuration provides a radial compression to the surrounding bone. Preferably the second portion 102C is provided with circumferential grooves 117, having an inner diameter 128 and an outer diameter 130. A drill may then be used having a diameter that is greater than the inner diameter 124 of screw thread 108 of first portion 102B, but less than the outer diameter 130 of second portion 102C of the cylindrical main body of the fixture, that is, 124<Drill Diameter<130. When fixture 100 is inserted into the drilled hole, the second portion 102C compresses the bone to some extent to impart initial stability. The wide diameter portion is located next to the flange so that the compressive action is more concentrated to the hard cortical part of the skull bone tissue.

As mentioned and illustrated in FIGS. 1 and 2, second portion 102C is preferably provided with circumferential grooves 117. In one embodiment, the inner diameter 128 also exceeds the inner diameter 124 of screw thread 108 of first portion 102B. Preferably the height 132 of the groove (130-128=132) is approximately ⅓ or less than the height of screw thread 108 of first portion 102B. In addition to the noted compressive action, such grooves may provide an increased retention between the fixture and the surrounding bone tissue, and spread the forces directed to the abutment more evenly in the bone.

This retention may also be improved by increasing the surface roughness of the bone contacting surfaces of fixture 100. For instance the surface may be modified by means of an abrasive blasting process according to WO 92/05745. In one embodiment the process is used to provide an average surface roughness Sa of about 0.2-2.0 μm, preferably 0.8-1.2 μm, and Sdr(2d/3d)=8-60%, preferably approximately 20-60%.

Circumferentially oriented grooves 117 may extend completely or partly around the periphery of the main body. In the embodiment shown in FIGS. 1 and 2 there are three separate grooves as an example. As an alternative, the grooves may be formed as a screw thread, which may have the same pitch as main screw thread 108, but having a inner diameter 128 that is greater than the inner diameter 124 of main screw thread 108, so that the height of the grooves 117 would be only approximately ⅓ or less of the height 134 of main screw thread 108 (126-124=134). In one embodiment, the extension of the second wide diameter portion 102C in the longitudinal direction of the fixture is about 15-25% of the total height of the fixture.

A method for inserting the fixture may comprise providing the anchoring fixture, drilling a hole, and inserting the anchoring fixture into the hole until the flange contacts the skull bone, wherein the hole has a diameter that is greater than the inner diameter of the first portion and less than the outer diameter of the second portion. No countersinking or removal of cortical bone is used which leaves more good bone left. When fixture 100 is inserted into such a drilled hole, the wider second portion of the fixture, that is, portion 102C next to the flange, provides a certain compression of the cortical bone on the radial direction of the prepared bone hole.

Further features and advantages of the present invention may be found in U.S. Provisional Application No. 60/951,169, entitled "Coupling Apparatus For a Bone Anchored Hearing Device," and filed Jul. 20, 2007, and U.S. Provisional Application No. 60/951,163, entitled "Bone Anchor Fixture for a Medical Prosthesis," and filed Jul. 20, 2007, which are hereby incorporated by reference herein.

The invention is not limited to the embodiment illustrated in the drawings but may be varied within the scope of the accompanying claims. Specifically, it is understood that other types of abrasive methods, coatings etc, may be used for increasing the roughness of bone-contacting surfaces. Such methods are known per se and not described here in any detail.

What is claimed is:

1. An anchoring fixture for anchoring a prosthesis to a skull bone comprising:
   a screw thread apparatus including a screw thread having a varying outer diameter;
   a flange configured to function as a stop for the anchoring fixture adapted to rest on top of the bone when the anchoring fixture is implanted into the bone; and
   a circumferential groove located, with respect to a side of the flange, on the anchoring fixture on a threaded side of the anchoring fixture,
   wherein the anchoring fixture is configured for anchoring a hearing prosthesis component to the skull bone at a location behind an external ear so that sound is transmitted from the hearing prosthesis via the skull bone to the cochlea.

2. The anchoring fixture of claim wherein:
   the anchoring fixture is tapered over at least a portion of a longitudinal length of the fixture.

3. The anchoring fixture of claim 1, wherein:
   the fixture comprises a material capable of integrating into surrounding bone tissue.

4. The anchoring fixture of claim 1, further comprising: a hexagonal interface to receive torque from a wrench.

5. The anchoring fixture of claim 4, wherein the flange includes a cylindrical portion.

6. The anchoring fixture of claim 1, further comprising:
   a self-tapping apparatus, wherein at least a portion of the screw thread apparatus is part of the self-tapping apparatus.

7. The anchoring fixture of claim 6, further comprising:
   wherein at least a portion of the screw thread apparatus includes cutting edges of the self-tapping apparatus.

8. A bone fixture configured to anchor to bone, comprising:
   a threaded tapered portion, wherein a maximum width of the bone fixture is about the same as a height of the bone fixture;
   a flange configured to function as a stop for the bone fixture adapted to rest on top of the bone when the bone fixture is implanted into the bone; and
   a circumferential groove located, with respect to a side of the flange, on the bone fixture on a threaded side of the bone fixture,
   wherein the bone fixture is configured to anchor a hearing aid prosthesis to a skull bone at a location behind an external ear of a recipient so that sound is transmitted from the hearing prosthesis via the skull bone to the cochlea.

9. The bone fixture of claim 8, wherein:
   the threaded tapered portion tapers towards a longitudinal axis of the bone fixture with distance towards a distal end of the bone fixture.

10. The bone fixture of claim 8, further comprising:
    an inner bore including an internal screw thread.

11. The bone fixture of claim 8, further comprising:
    a portion configured to interface with an insertion tool so that torque can be transferred from the insertion tool to the bone fixture, wherein the portion includes an interface section in the form of a hex.

12. The bone fixture of claim 8, further comprising:
    a self-tapping apparatus, wherein a thread of the tapered threaded portion includes first discontinuities forming respective cutting edges of the self-tapping apparatus and second discontinuities forming respective relief areas of the self-tapping apparatus, wherein the relief areas and the cutting edges are provided in an alternating configuration around a body of the bone fixture.

13. The bone fixture of claim 8, wherein:
    a thread of the tapered threaded portion includes a first discontinuity forming a first cutting edge, a second discontinuity forming a relief area, and a third discontinuity forming a second cutting edge, wherein the relief area is, with respect to position along the thread, between the first cutting edge and the second cutting edge.

14. The bone fixture of claim 8, wherein:
    the circumferential groove is located between the flange and all threads of the fixture.

15. An anchoring fixture for anchoring a hearing prosthesis to a cranial section of a skull bone comprising:
a main body configured to be implanted into the bone, the main body comprising a distal tapered apical portion and a non-tapered first portion adjacent to the distal tapered apical portion and a non-tapered second portion adjacent to the first portion;
a flange configured to function as a stop for the anchoring fixture adapted to rest on top of the bone when the anchoring fixture is implanted into the bone; and
a circumferential groove located, with respect to a side of the flange, on the anchoring fixture on a main body side of the anchoring fixture, wherein
the first portion has a first outer diameter and the second portion has a second outer diameter, and
the first outer diameter is greater than the second outer diameter.

16. The anchoring fixture of claim 1, wherein:
the screw thread includes an inner diameter that remains about constant over about at least two turns of the screw thread.

17. The anchoring fixture of claim 1, wherein:
a cross-section of the fixture lying on and parallel to a longitudinal axis of the anchoring fixture has, on one side, with respect to location from a proximal end to a distal end of the fixture, starting at a location of maximum screw thread radius on the one side, six turns inclusive of the turn having the maximum screw thread radius.

18. The anchoring fixture of claim 1, wherein:
the screw thread has a diameter that decreases with location along a longitudinal axis of the anchoring fixture, which decrease is non-linear.

19. The anchoring fixture of claim 1, wherein:
the screw thread has a diameter that decreases with location along a longitudinal axis of the anchoring fixture, which decrease is geometric.

20. The anchoring fixture of claim 1, wherein:
a cross-section of the fixture lying on and parallel to a longitudinal axis of the anchoring fixture has, on one side, with respect to location from a proximal end to a distal end of the fixture, starting at a location of maximum screw thread radius on the one side, turns that progressively have decreasing radius with each turn.

21. The bone fixture of claim 8, wherein:
a cross-section of the fixture lying on and parallel to a longitudinal axis of the bone fixture has, on one side, with respect to location from a proximal end to a distal end of the fixture, starting at a location of maximum screw thread radius on the one side, turns that progressively have decreasing radius with each turn.

22. The anchoring fixture of claim 1, wherein:
an outer diameter of the screw thread tapers over at least a portion of a longitudinal length of the fixture, and, with respect to a cross-section of the fixture lying on and parallel to a longitudinal axis of the anchoring fixture, the fixture has, on one side, with respect to a direction from a proximal end to a distal end of the fixture along the tapered portion, crests of the threads of the taper portion that are flat, and a distance of respective flats in the longitudinal direction on that one side becomes progressively larger with respect to location closer to the distal end of the fixture.

23. The anchoring fixture of claim 1, wherein:
an outer diameter of the screw thread tapers over at least a portion of a longitudinal length of the fixture and, with respect to a cross-section of the fixture lying on and parallel to a longitudinal axis of the anchoring fixture, the fixture has, on one side, with respect to a direction from a proximal end to a distal end of the fixture along the tapered portion, crests of the threads of the taper portion that are flat such that a more distal thread has a larger flat distance in the longitudinal direction than a thread immediately proximal thereto.

24. The anchoring fixture of claim 1, wherein:
a cross-section of the fixture lying on and parallel to a longitudinal axis of the anchoring fixture has, on one side, a plurality of thread turns, every turn from a turn with the largest radius to a distal turn on that one side having a flat crest.

25. The anchoring fixture of claim 1, wherein:
the circumferential groove has an inner diameter that exceeds an inner diameter of at least three turns of tapered threads.

26. The anchoring fixture of claim 1, wherein:
the circumferential groove has an outer diameter that exceeds an inner diameter of all of the turns of the threads.

27. The anchoring fixture of claim 1, wherein:
the fixture includes a surface configured to contact bone when the fixture is implanted into bone having an average surface roughness Sa of about 0.2-2.0 µm.

28. The anchoring fixture of claim 1, wherein:
a portion of a surface of the fixture that contacts bone has a modified increased surface roughness relative to another portion of the surface of the fixture that contacts bone.

29. The anchoring fixture of claim 1, wherein:
a maximum width of the fixture is less than a maximum length of the fixture;
a maximum diameter of the screw thread apparatus is between 3.5 and 5 mm;
a length from a bottom of the flange to a distal end of the anchoring fixture is no greater than 5 mm, the screw thread apparatus and the distal end being on a same side of the flange;
a maximum diameter of the flange is greater than the length from the bottom of the flange to a distal end of the anchoring fixture; and
the maximum diameter of the flange has a value that exceeds a peak diameter of the thread by approximately 10-20%.

30. The anchoring fixture of claim 29, wherein:
a cross-section of the fixture lying on and parallel to a longitudinal axis of the anchoring fixture has, on one side, a plurality of thread turns, every turn from a turn with the largest radius to a most distal turn on that one side having a flat crest;
the circumferential groove has an inner diameter that exceeds an inner diameter of most of the turns of the thread; and
a portion of a surface of the fixture that contacts bone has a modified increased surface roughness relative to another portion of the surface of the fixture that contacts bone.

31. The anchoring fixture of claim 29, wherein:
the screw thread includes an inner diameter that remains at least about constant over at least some of the turns of the screw thread;
a cross-section of the fixture lying on and parallel to a longitudinal axis of the anchoring fixture has, on one side, with respect to location from a proximal end to a distal end of the fixture, starting at a location of maximum screw thread radius on the one side, six turns inclusive of a turn having the maximum screw thread radius;

the screw thread has a diameter that decreases with location along the longitudinal axis, which decrease is non-linear;

the outer diameter of the screw thread tapers over at least a portion of a longitudinal length of the fixture and, with respect to a cross-section of the fixture lying on and parallel to the longitudinal axis, the fixture has, on one side, with respect to a direction from a proximal end to a distal end of the fixture along the tapered portion, crests of the threads of the taper portion that are flat, and the distance of respective flats in the longitudinal direction on that one side becomes progressively larger with respect to location closer to the distal end of the fixture.

32. The anchoring fixture of claim 29, wherein:

a maximum width of the fixture is within about 10% of a maximum length of the fixture.

33. The anchoring fixture of claim 1, wherein:

a maximum diameter of the screw thread apparatus is between 3.5 and 5 mm, and a length from a bottom of the flange to a distal end of the anchoring fixture is no greater than 5 mm, the screw thread apparatus and the distal end being on a same side of the flange.

34. The anchoring fixture of claim 1, wherein:

a maximum diameter of the flange is greater than a length from a bottom of the flange to a distal end of the anchoring fixture, the screw thread apparatus and the distal end being on a same side of the flange.

35. The anchoring fixture of claim 1, wherein:

the anchoring fixture includes a means for exerting a compression onto the skull bone in a radial direction to stabilize the fixture in the skull bone.

36. The anchoring fixture of claim 29, wherein:

the anchoring fixture includes a means for exerting a compression onto the skull bone in a radial direction to stabilize the fixture in the skull bone.

37. The anchoring fixture according to claim 1, wherein:

the flange has a maximum diameter that exceeds a peak diameter of the thread by approximately 10-20%.

38. The anchoring fixture of claim 1, wherein:

the circumferential groove is located between the flange and all threads of the fixture.

39. The bone fixture of claim 8, wherein:

the bone fixture is configured to apply more radially compressive force on surrounding bone during implantation at a first location of the bone fixture below the flange relative to a second location of the bone fixture, wherein the second location is at a distal end of the bone fixture, the screw thread apparatus being on the same side of the flange as the distal end.

40. The anchoring fixture of claim 1, wherein:

a surface of a first portion of the bone fixture below the flange has a surface roughness that is greater than that of a second portion, the second portion including the circumferential groove.

41. The bone fixture of claim 8, wherein:

a surface of a first portion of the bone fixture below the flange is a modified surface that increases surface roughness, the first portion being separate from a second portion that includes the circumferential groove, wherein the roughness of the first portion is greater than that of the second portion.

42. The bone fixture of claim 8, wherein:

the bone fixture includes a tapered portion that establishes a seat for a skin-penetrating abutment to create a connecting fit between the fixture and the abutment.

43. The bone fixture of claim 8, wherein:

the bone fixture comprises an implantation means for securing the fixture onto the skull bone without completely penetrating through the skull bone.

44. The bone fixture of claim 42, wherein:

the implantation means comprises a compression means for exerting a compression onto the skull bone in a radial direction to stabilize the fixture in the skull bone.

45. The bone fixture of claim 8, wherein:

a maximum diameter of the threaded portion is between 3.5 and 5 mm, and a length from a bottom of the flange to a distal end of the bone fixture is no greater than 5 mm, the threaded portion and the distal end being on a same side of the flange.

46. The bone fixture of claim 8, wherein:

the threaded portion extends from the circumferential groove to a distal end of the fixture.

47. The bone fixture of claim 8, wherein:

the flange has a maximum diameter that exceeds a peak diameter of a thread of the threaded taper portion by approximately 10-20%.

48. The anchoring fixture of claim 1, wherein:

a maximum width of the fixture is slightly less than a maximum length of the fixture.

\* \* \* \* \*

UNITED STATES PATENT AND TRADEMARK OFFICE
CERTIFICATE OF CORRECTION

PATENT NO. : 9,838,807 B2
APPLICATION NO. : 14/922604
DATED : December 5, 2017
INVENTOR(S) : Lars Jinton, Erik Holgersson and Peter Elmberg Page 1 of 1

It is certified that error appears in the above-identified patent and that said Letters Patent is hereby corrected as shown below:

In the Claims

Column 6, Line 4, should read as follows:
2. The anchoring fixture of claim 1, wherein:

Column 6, Line 18, should read as follows:
7. The anchoring fixture of claim 6,

Column 8, Line 42, should read as follows:
length from the bottom of the flange to the distal end of Column 9, Line 6, should read as follows:
non-linear; and Signed and Sealed this
Fourteenth Day of August, 2018

Andrei Iancu
*Director of the United States Patent and Trademark Office*

(12) INTER PARTES REVIEW CERTIFICATE (2329th)
United States Patent
Jinton et al.

(10) Number: US 9,838,807 K1
(45) Certificate Issued: Sep. 2, 2021

(54) BONE ANCHOR FIXTURE FOR A MEDICAL PROSTHESIS

(71) Applicants: Lars Jinton; Erik Holgersson; Peter Elmberg

(72) Inventors: Lars Jinton; Erik Holgersson; Peter Elmberg

(73) Assignee: COCHLEAR LIMITED

Trial Number:

IPR2019-00975 filed Apr. 15, 2019

Inter Partes Review Certificate for:

Patent No.: 9,838,807
Issued: Dec. 5, 2017
Appl. No.: 14/922,604
Filed: Oct. 26, 2015

The results of IPR2019-00975 are reflected in this inter partes review certificate under 35 U.S.C. 318(b).

INTER PARTES REVIEW CERTIFICATE
U.S. Patent 9,838,807 K1
Trial No. IPR2019-00975
Certificate Issued Sep. 2, 2021

AS A RESULT OF THE INTER PARTES REVIEW PROCEEDING, IT HAS BEEN DETERMINED THAT:

Claims 1-12, 14, 16, 17, 25, 28, 33-35, 37-41 and 45-47 are found patentable.

\* \* \* \* \*